United States Patent [19]

Fischer et al.

[11] 4,416,997
[45] Nov. 22, 1983

[54] PYRIDINE-FREE KARL FISCHER REAGENT USEFUL IN DETERMINING WATER

[75] Inventors: Wolfgang Fischer, Darmstadt; Karl-Dieter Krenn, Pfungstadt, both of Fed. Rep. of Germany

[73] Assignee: Merck Patent Gesellschaft mit beschränkter Haftung, Darmstadt, Fed. Rep. of Germany

[21] Appl. No.: 333,100

[22] Filed: Dec. 21, 1981

[30] Foreign Application Priority Data

Dec. 20, 1980 [DE] Fed. Rep. of Germany ....... 3048237

[51] Int. Cl.$^3$ .................... G01N 31/16; G01N 27/42; G01N 33/18; C09K 3/00
[52] U.S. Cl. .................................................. 436/42
[58] Field of Search ........................... 252/408; 436/42

[56] References Cited

U.S. PATENT DOCUMENTS 3,974,258  8/1976  Poitevin et al. .................... 423/242
4,295,990  10/1981  Verbeek et al. .................... 252/408

FOREIGN PATENT DOCUMENTS 728947  4/1955  United Kingdom .

OTHER PUBLICATIONS

Verhoef et al., Analytica Chimica Acta, vol. 94, pp. 395–403, (1977).

Primary Examiner—Benjamin R. Padgett
Assistant Examiner—Margaret Moskowitz
Attorney, Agent, or Firm—Millen & White

[57] ABSTRACT

An essentially pyridine-free Karl Fischer reagent useful in the determination of water, comprises a dissolving agent containing sulfur dioxide and a pyridine substitute in a Karl Fischer solvent, and a titrating agent containing iodine in a Karl Fischer solvent, wherein the pyridine substitute is an alkali or alkaline earth metal benzoate or ammonia, and the reagent is essentially free of pyridine.

12 Claims, No Drawings

PYRIDINE-FREE KARL FISCHER REAGENT USEFUL IN DETERMINING WATER

BACKGROUND OF THE INVENTION

The present invention relates to a pyridine-free Karl Fischer reagent for the determination of water. The reagent comprises a dissolving agent for the sample to be investigated and a titrating agent. This invention also relates to a process for the determination of water using this reagent. The dissolving agent contains sulfur dioxide and a pyridine substitute in a solvent, and the titrating agent contains iodine in a solvent.

A number of proposals for replacing pyridine in the Karl Fischer reagent by other substances is known from the literature. In Anal. Chim. Acta 94, 395 (1977), sodium acetate is used as a substitute for pyridine. However, this entails certain disadvantages. Acetates are formed, for example, with the alcohol used as the solvent, water being liberated and naturally interfering with the water determination method. The solutions are therefore unstable and their blank values increase constantly.

In addition to acetates, alcoholates, phenolates and salts of weak organic acids are also mentioned as a substitute for pyridine in British Pat. No. 728,947. When the substances mentioned in this patent were checked, it was found that they are unsuitable as a pyridine substitute, partly because of insufficient solubility and partly because of inadequate stability of the prepared solutions. Furthermore, it is known that when pyridine is replaced by amines, stable end points cannot be obtained in the titration (Anal. Chem. 28, 1,116 (1956).

It is thus found from the state of the art that the replacement of pyridine by the mentioned compounds is not practical, since these reagents either are not sufficiently soluble or are unstable, or yield false results.

SUMMARY OF THE INVENTION

It is thus an object of this invention to provide a pyridine-free Karl Fischer reagent which is stable and enables exact analytical results.

Upon further study of the specification and appended claims, further objects and advantages of this invention will become apparent to those skilled in the art.

Surprisingly, it has been found that a Karl Fischer reagent which yields a stable and exact end point can be obtained if benzoate or ammonia is used as the pyridine substitute. These substances have a very good solubility in the reagent solution, react with alcohols virtually without the formation of esters, and have a very high stability in storage.

This invention in one aspect thus, provides a pyridine-free Karl Fischer reagent for the determination of water, comprising a dissolving agent containing sulfur dioxide and a pyridine substitute in a solvent, and a titrating agent containing iodine in a solvent, wherein the pyridine substitute is benzoate or ammonia.

The present invention also relates to a process for the determination of water using this pyridine-free Karl Fischer reagent.

DETAILED DESCRIPTION

The pyridine-free Karl Fischer reagent consists of two solutions, a dissolving agent and a titrating agent. The dissolving agent contains sulfur dioxide and a pyridine substitute in a solvent and is used for taking up the sample to be investigated with respect to its water content. The molar ratio of pyridine substitute to sulfur dioxide is about 2:1 to about 1:2, preferably about 1:1. The titrating agent is a solution which is adjusted to a constant titer and which consists of iodine in a solvent. However, dissolving agent and titrating agent can also be combined even before the titration. The reagent thus obtained is sufficiently stable to be employed in the customary manner as a titrating liquid. The process is particularly advantageous when the substance to be investigated has a better solubility in another solvent than in the solvent contained in the dissolving agent. In this case, the reaction rate is also not dependent on the solubility rate.

The alkali metal and alkaline earth metal salts of benzoic acid, such as sodium, potassium, magnesium, calcium, strontium and barium benzoate, preferably sodium and potassium benzoate, as well as ammonia, are suitable substitutes for pyridine in the reagent of this invention. A comparison between a dissolving agent which contains sodium acetate, sulfur dioxide and methanol and dissolving agents which contain sodium benzoate instead of sodium acetate shows that the water content of the particular solutions, when these solutions are boiled under reflux, increased, after 220 hours, from 0.064 to 0.47% in the case of the solution containing sodium acetate, while the water content in the case of the benzoate agent increased, in contrast, only from 0.051 to 0.056%. The use of ammonia as a pyridine substitute also has a number of advantages: the reagent is stable, undergoes no reaction with the solvent, and reacts much more rapidly than a solution containing pyridine.

All solvents described for this purpose, i.e., for Karl Fischer reagents, in the literature, preferably alcohols and/or glycols, particularly lower alcohols, e.g., of 1–6 C atoms, such as methanol, ethanol, propanol etc., as well as ethylene glycol and ethylene glycol mono-$C_3$-alkyl ethers, are suitable as solvents both for the dissolving agent and for the titrating agent. The solvents can be used individually or in any desired mixing ratio. Thus, for example, it is possible to dissolve the pyridine substitute of this invention in an alcohol and the iodine in a glycol, or both in any desired mixing ratio of alcohols, glycols or mixtures of both solvent types.

With the pyridine-free Karl Fischer reagent of this invention, the end point of the volumetric water determination can be determined visually, photometrically or electrometrically (dead stop method, coulometric method). The reagent is suitable both for use in automatic titrating apparatuses and as a field method, the field method first having been made possible by the replacement of the methanol by the stated solvents with a low vapor pressure.

A number of advantages are obtained by replacing pyridine by the compounds mentioned: the change at the end point is clearer than with the conventional Karl Fischer reagents, the reagent is less toxic and is altogether less of a pollutant and is cheaper.

The titration is effected in general, with the exclusion of atmospheric moisture. In the case of the visual titration, the titration is carried out up to the color change from colorless to yellow. However, visual and photometric titrations are impossible if the solution to be analyzed has a strong color of its own. The electrometric titration, particularly the so-called dead stop method, is therefore now preferred. This process is based on a deliberately produced polarization at two identical platinum electrodes. When a small potential difference is applied, the voltage resulting from the polarization is compensated and the current flow is interrupted. The end point of the titration is indicated by a strong deflection of the galvanometer which subsequently remains unchanged at a fixed point, this process being based on the sharp transition from polarization or depolarization of one electrode to complete depolarization or polarization of both electrodes.

Unless indicated otherwise herein all details of the Karl Fischer reagent and titrations of this invention are fully conventional and disclosed, e.g., in J. Amer. Chem. Soc. 61, 2407 (1939), whose disclosure is incorporated by reference herein.

Without further elaboration, it is believed that one skilled in the art can, using the preceding description, utilize the present invention to its fullest extent.

The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

For the preparation of the dissolving agent and the titrating agent, the particular substances were dissolved in the appropriate solvent as shown below:
(a)
Dissolving agent
160 g of sulfur dioxide (2.5 M) and
720 g of sodium benzoate (5.0 M) in 5 l of methanol
(b)
Titrating agent
250 g of iodine in 5 l of methanol The substance to be investigated for its water content was dissolved, according to the estimated water content, in 20 ml of the dissolving agent, and was titrated to the end point with the titrating agent, while stirring continuously and with the exclusion of atmospheric moisture.

EXAMPLE 2

The following Karl Fischer solutions were prepared:
(a)
Dissolving agent
64 g of sulfur dioxide (1.0 M) and
144 g of sodium benzoate (1.0 M) in 1 l of ethylene glycol monomethyl ether
(b)
Titrating agent
50 g of iodine in 1 l of ethylene glycol monomethyl ether The same results were achieved with these solutions as with the solutions according to Example 1. The results also do not change after partial or complete replacement of the ethylene glycol monomethyl ether by methanol or propanol.

EXAMPLE 3

The following solutions were used for carrying out a coulometric water determination:
(a)
Cathode solution
64 g of sulfur dioxide (1.0 M) and
144 g of sodium benzoate (1.0 M) in 1 l of methanol
(b)
Anode solution
analogous, but with the addition of 5 to 10 g of iodine.

EXAMPLE 4

The following Karl Fischer solutions were prepared:
(a)
Dissolving agent
From two gas cylinders, each of which was standing on a balance
640 g of sulfur dioxide (10.0 M) and
170 g of ammonia (10.0 M)
were simultaneously passed into 10 l of methanol.
(b)
Titrating agent
500 g of iodine in 10 l of methanol The substance to be investigated for its content was dissolved in 20 ml of the dissolving agent and was titrated to the end point with the titrating agent, while stirring and with the exclusion of atmospheric moisture. The same results were obtained if methanol was partially or completely replaced by ethylene glycol monomethyl ether.

EXAMPLE 5

Dissolving agent and titrating agent are prepared analogously to Example 4, the dissolving agent containing 85 g of ammonia instead of 170 g of ammonia. The two solutions were combined before the titration. The substance to be investigated for its water content was dissolved in 20 ml of a solvent and was titrated with the solution containing the dissolving agent and titrating agent.

EXAMPLE 6

A Karl Fischer solution was prepared which contained, in 1 l of ethylene glycol monomethyl ether,
128 g of sulfur dioxide (2.0 M),
30.6 g of ammonia (1.8 M) and
127 g of iodine (0.5 M).

The sample solution to be investigated with respect to its water content, as such or dissolved in ethylene glycol monomethyl ether, was titrated to the end point, while stirring continuously and with the exclusion of atmospheric moisture. With this prepared solution, it was possible to carry out water determinations which contained up to 5.4 mg of water per ml of sample solution.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An essentially pyridine-free Karl Fischer reagent useful in the determination of water, comprising a dissolving agent containing sulfur dioxide and a pyridine substitute in a Karl Fischer solvent, and a titrating agent containing iodine in a Karl Fischer solvent, wherein the pyridine substitute is an alkali or alkaline earth metal benzoate or ammonia, and the reagent is essentially free of pyridine.

2. An essentially pyridine-free Karl Fischer reagent of claim 1, wherein the molar ratio of pyridine substitute to sulfur dioxide is about 2:1 to about 1:2.

3. An essentially pyridine-free Karl Fischer reagent of claim 1 or 2 wherein the pyridine substitute is sodium or potassium benzoate or ammonia.

4. An essentially pyridine-free Karl Fischer reagent of claim 1 wherein the solvents for each agent independently are a lower alcohol or glycol or an ethylene glycol mono-$C_3$-alkylether.

5. A method for the determination of water comprising analyzing a sample for water content using a pyridine-free Karl Fischer reagent wherein said reagent is that of claim 1 or 2.

6. A method of claim 5 wherein the analysis is performed photometrically or electrometrically.

7. An essentially pyridine-free Karl Fischer reagent of claim 1 wherein the pyridine substitute is an alkali metal benzoate.

8. An essentially pyridine-free Karl Fischer reagent of claim 1 wherein the pyridine substitute is an alkaline earth metal benzoate.

9. An essentially pyridine-free Karl Fischer reagent of claim 1 wherein the pyridine substitute is ammonia.

10. An essentially pyridine-free Karl Fischer reagent of claim 1 wherein the pyridine substitute is an alkali or alkaline earth metal benzoate.

11. An essentially pyridine-free Karl Fischer reagent of claim 1 wherein the molar ratio of pyridine substitute to sulfur dioxide is about 1:1.

12. An essentially pyridine-free Karl Fischer reagent of claim 1 wherein the dissolving agent and the titrating agent are combined in a single reagent.

* * * * *